United States Patent [19]

Bison et al.

[11] 4,426,531
[45] Jan. 17, 1984

[54] PROCESS FOR THE PREPARATION OF 1H-TETRAZOLE-1 COMPOUNDS USING TRIMETHYLSILYL AZIDE

[75] Inventors: Günter Bison, Troisdorf-Sieglar; Norbert Linkat, St. Augustin; Wolfgang Wolfes, Niederkassel-Mondorf, all of Fed. Rep. of Germany

[73] Assignee: Dynamit Nobel Aktiengesellschaft, Troisdorf, Fed. Rep. of Germany

[21] Appl. No.: 323,013

[22] Filed: Nov. 19, 1981

Related U.S. Application Data

[63] Continuation of Ser. No. 102,080, Dec. 10, 1979, abandoned.

[30] Foreign Application Priority Data

Dec. 14, 1978 [DE] Fed. Rep. of Germany ....... 2854015

[51] Int. Cl.³ .......................................... C07D 257/04
[52] U.S. Cl. ....................................... 548/253; 544/27
[58] Field of Search ......................................... 548/253

[56] References Cited

U.S. PATENT DOCUMENTS 3,767,667 10/1973 Kamiya et al. ..................... 548/253

OTHER PUBLICATIONS

Birkofer et al., Chem. Berichte, 96, 2754, (1963).
Taylor, Adv. in Org. Chem., vol. 8, pp. 146–155, Interscience N.Y., N.Y., (1972).
Rodd, Chem. of Carbon Compounds, vol. IV pt A, Heterocyclic Compounds, Elsevier, N.Y., 1957, pp. 440–481.

*Primary Examiner*—Donald G. Daus
*Assistant Examiner*—David B. Springer
*Attorney, Agent, or Firm*—Sprung, Horn, Kramer & Woods

[57] ABSTRACT

A process for the preparation of 1H-tetrazole-1-acetic acid or its ester which comprises contacting trimethylsilyl azide with an orthocarboxylic acid ester of the formula $$R_1C(OR)_3$$

wherein
$R_1$ is hydrogen or $C_{1-8}$ alkyl,
R is alkyl and glycine, an ester thereof, a salt thereof or an ester hydrochloride or the resultant imino ether obtained from reaction of glycine, its ester or salt and the orthocarboxylic acid ester.

6 Claims, No Drawings

PROCESS FOR THE PREPARATION OF 1H-TETRAZOLE-1 COMPOUNDS USING TRIMETHYLSILYL AZIDE

This is a continuation, of application Ser. No. 102,080, filed Dec. 10, 1979, abandoned.

The present process relates to the improved and simplified preparation of tetrazole compounds, and especially the preparation of tetrazole acetic acid and its esters.

It is known that many amino compounds can be reacted with orthocarboxylic acids to give imino ethers. (De Wolfe: Carboxylic Ortho Acid Derivatives, Academic Press [1970], pages 178 to 184.) According to Hagedorn et al. (Berichte 99 [1960], pages 850 to 855), such imino ethers are capable of forming with hydrazoic acid or its metal salts 1H-tetrazole derivatives.

These reactions do not proceed smoothly. The yield of imino ethers frequently is low and they decompose readily. The yields of tetrazole derivatives therefore are consistently low.

In German patent application DOS No. 21 47 023 it is proposed to add the metal salts of hydrazoic acid, and especially sodium azide, already during the formation of the imino ethers in the presence of acetic acid, in particular, as solvent. However, this process, too, is difficult to carry out and results in low yields.

Hydrazoic acid is known to be highly explosive and requires precautionary measures against detonations even when used in very small amounts.

When metal azides such as sodium azide, which is not an explosion hazard, are used, condensation to the tetrazole compound will occur only when an acid medium is used. In accordance with the law of mass action, metal azides will, in the presence of acetic acid, for example, continuously release $HN_3$, which in the process of German application DOS No. 21 47 023, is to be regarded as the actual reactant.

Accordance to Example 5 of said German application, an $HN_3$ concentration of 16 percent is measured in the gas space, which is sufficient to detonate the gas phase, and with it the entire batch. However, it is not possible to resort to the use of nonacidic solvents. When dimethylformamide, for example, is used, the yields drop practically to zero and the HCl, bound in saltlike manner, of the aminohydrochlorides used will not improve the yield, either.

Thus, it has evidently not been possible to overcome the drawback of detonability in preparation, since $HN_3$ itself apparently is the essential reactant in the formation of the tetrazole ring.

SUMMARY OF THE INVENTION

It has now been found that tetrazole compounds can be produced in high yields without the intermediate formation of hydrozoic acid.

In accordance with the invention, tetrazole compounds are formed in high yields without formation of intermediate hydrazoic acid by a process comprising contacting trimethylsilyl azide with an orthocarboxylc acid ester of the formula $R_1C(OR)_3$ wherein $R_1$ is hydrogen or $C_{1-8}$ alkyl and R is alkyl and glycine, an ester thereof, a salt thereof or an ester hydrochloride or the resultant imino ether obtained from reaction of glycine, its ester or salt and the orthocarboxylic acid ester.

As a result, one obtains good yields of 1H-tetrazole-1-acetic acid or its esters.

It is surprising that the nonpolar compound trimethylsilyl acid brings about the desired ring closure and, in addition, provides high yields.

The great advantage is that trimethylsilyl azide is a compound that is not an explosion hazard. The conversion of trimethylsilyl azide to tetrazole compounds proceeds without the liberation of hydrazoic acid even when acidic solvents such as acetic acid or hydrochlorides of amino compounds are present. Thus there is no likelihood of a detonation in the reaction with trimethylsilyl azide. The preparation of trimethylsilyl also proceeds without the liberation of $HN_3$.

The present process may be used to prepare numerous tetrazole compounds which may have substituents or bridge-type crosslinks on the nitrogen deriving from the amine, or on the carbon of the ring, and possibly also on the other nitrogen atoms.

However, it is preferred, in the preparation of 1H-tetrazole-1-acetic acid or its esters to employ lower alkyl esters having from 1 to 8 carbon atoms, especially those having from 1 to 2 carbon atoms, of glycine.

The starting material amino compounds and orthocarboxylic acid esters, as such, and known are are described in the literature cited. The orthocarboxylic acid esters can be represented by the formula

wherein $R_1$ is hydrogen or $C_{1-8}$ alkyl, and R is alkyl.

Suitable amino compounds for the preparation of tetrazole acetic acid and its esters are glycine, its alkyl esters and salts, especially the ester hydrochlorides.

Suitable orthocarboxylic acid esters are primarily orthoformic acid esters or orthoacetic acid esters, particularly the ethyl esters, and more particularly, the methyl esters. Trimethylsilyl azide can readily be prepared, in yields of about 98 percent by the process described in German Offenlegungsschrift No. 19 65 741, the disclosure of which is hereby incorporated herein by reference.

$R_1$ thus is preferably H or $CH_3$, and R, $-CH_3$ or $-C_2H_5$. One can first react the amino compound and the ortho ester in order to obtain the corresponding imino ether and then react the latter with trimethylsilyl azide, optionally in a separate reaction. However, it is decidedly preferred to let both reactions proceed at the same time by appropriate metering in of the amino compound, the ortho ester and the trimethylsilyl azide.

It is, moreover, of considerable advantage to carry out the preparation of the trimethylsilyl azide immediately prior to the preparation of the tetrazole compound.

The molar amounts of glycine ester and trimethylsilyl azide generally should be in a stoichiometric ratio. However, the ortho ester is desirably present in a stoichiometric excess which preferably ranges from at least 50 mol percent to as much as 300 mol percent excess.

The mol ratio of orthocarboxylic acid ester to glycine compound is 1 to 300:1, preferably 2 to 5:1. The mol ratio of orthocarboxylic acid ester to trimethylsilyl azid is 1 to 300:1, preferably 2 to 5:1.

The process should be carried out at temperatures ranging from 50° to 100° C. in general, and from 65° to 80° C. in particular. The reaction is generally carried out under the partial pressures of the reactants in a vessel with a reflux condenser. However, it may also be carried out in a closed vessel under partial pressure. Generally, when the process is conducted in a closed vessel, it is carried out at a pressure from as low as 760 Torr up to 3 atmospheres.

These conditions apply as well where the orthocarboxylic acid reacts initially with the glycine compounds and the resultant imino ether is reacted with subsequently added trimethylsilyl azide.

The yield usually is over 90 percent, and often as high as 95 percent, bason on the trimethylsilyl azide. This shows that surprisingly, the nonpolar compound trimethylsilyl azide, which is not capable of forming free $HN_3$, can also give high yields of tetrazole compounds which even exceed those of prior art processes.

The preferred solvents are aliphatic carboxylic acids, and particularly acetic acid, although in special cases other inert solvents known from the literature may be used.

Under the conditions of preparation specified, tetrazole compounds, and particularly tetrazole acetic acid and its esters, are obtained in very good purities of at least 95 percent or better.

1H-Tetrazole-1-acetic acid and its esters may be used as side chain of Cefazolin of the formula

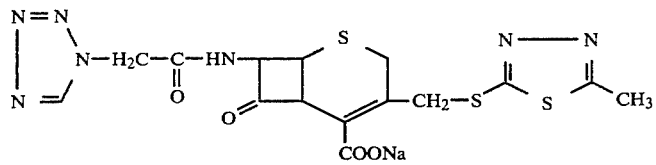

an antibiotic effective substance of the Cefalosporine group, more specific described by "The Merck Index, Encyclopedia of Chemicals and Drugs" published by Merck and Co. Inc. 9. Edition (1976) Nr. 1911; Woodward et al: J. Am. Chem. Soc. 88 (1966) 852 and Chaurette et al: J. Am. Chem. Soc. 84 (1962) 3401.

PREPARATION OF TRIMETHYLSILYL AZIDE 22.8 liters (19.38 kg=0.18 K mol) trimethylchlorosilane is charged to a 400 liter enameled vessel with agitator, reflux condenser and metering device, then 640 g N-methyl-pyrrolidone is added as catalyst along with 12.7 kg (0.19 K mol) $NaN_3$ and the mixture is heated to 50° C. over a period of one hour with weak reflux. Over another two hours, the temperature is slowly raised to 95° C., which is the boiling point of trimethylsilyl azide. Conversion after about 30 minutes with an internal temperature of 95° C. and with reflux is about 98 percent, as determined by gas chromatography.

In order to more fully illustrate the nature of the invention and the manner of practicing the same, the following examples are presented:

EXAMPLE 1

After the solution prepared as outlined above from trimethylsilyl azide has been cooled to about 40° C., there are added 51.1 kg (0.49 K mol) trimethyl orthoformate, 56.1 kg acetic acid, 14.6 kg anhydrous sodium acetate, and 25 kg (0.18 K mol) glycine ethyl ester hydrochloride. The mixture is slowly heated to 70° C. with agitation and maintained at that temperature for 3 hours. After working up through solvent extraction, 27.02 kg tetrazole acetic acid (TAA) ester with a purity of 95 percent is obtained. At room temperature, the initially oily ester crystallizes out completely. The yield was 96.2 weight percent, based on the trimethylsilyl azide.

The ester so obtained can be saponified to the free 1H-tetrazole-1-acetic acid without aftertreatment.

The separated water phase is free of produce and can be disposed of without danger by combustion.

EXAMPLE 2

Analogously to Example 1, but with a temperature of 55° C., a corresponding result is obtained after a reaction time of 5.5 hours.

EXAMPLE 3

Analogously to Example 1, but at 100° C., TAA-1-acetic acid ester is again obtained in good yield and purity.

EXAMPLE 4

Analogously to Example 1, but using 0.51 K mol triethylorthoformate as ortho ester, TAA acetic acid ester is obtained with corresponding results.

EXAMPLE 5

Analogously to Example 1, but using the corresponding molar amount of glycine methylester hydrochloride, TAA-1-acetic acid methylester is likewise obtained in a yield of over 90 percent.

What is claimed is:

1. A process for the preparation of 1H-tetrazole-1-acetic acid or its methyl or ethyl ester which comprises the steps of reacting trimethylsilyl azide with an orthocarboxylic acid ester of the formula $$R_1C(OR)_3$$

wherein
$R_1$ is hydrogen or $C_{1-8}$alkyl,
R is lower alkyl
and glycine or a methyl or ethyl ester thereof, or methyl or ethyl ester hydrochloride.

2. A process for the preparation of 1H-tetrazole-1-acetic acid or its esters according to claim 1 wherein trimethylsilyl azide is formed immediately prior to the preparation of the tetrazole compound.

3. A process according to claim 1 wherein said trimethylsilyl azide contacts an imino ether obtained from reaction of glycine, its ester or salt with said orthocarboxylic acid ester.

4. A process according to claim 1 wherein trimethylsilyl azide contacts said glycine, its ester or salt and said orthocarboxylic acid ester.

5. A process according to claim 1 wherein the reaction is conducted at a temperature of 50° to 100° C.

6. A process according to claim 1, carried out without the intermediate formation of hydrazoic acid.

* * * * *